United States Patent [19]

Norlien et al.

[11] Patent Number: 4,995,256
[45] Date of Patent: Feb. 26, 1991

[54] ZIRCONIA CELL $O_2$ SENSOR FOR RESPIRATORY GAS ANALYSIS

[75] Inventors: John A. Norlien, St. Paul; James M. Huhn, Arden Hills, both of Minn.; A. Gerrit Crawford, San Francisco, Calif.

[73] Assignee: Medical Graphics Corporation, St. Paul, Minn.

[21] Appl. No.: 326,100

[22] Filed: Mar. 20, 1989

[51] Int. Cl.$^5$ ............................................. G01N 27/12
[52] U.S. Cl. ..................................... 73/31.04; 128/34; 73/31.05
[58] Field of Search ................. 73/23; 338/34; 422/98

[56] References Cited

U.S. PATENT DOCUMENTS

| 4,225,842 | 9/1980 | Schlesselman et al. | 73/23 X |
| 4,283,256 | 8/1981 | Howard et al. | 73/23 X |
| 4,532,492 | 7/1985 | Esper et al. | 73/23 X |
| 4,535,316 | 8/1985 | Wertheimer et al. | 73/23 X |

Primary Examiner—Hezron E. Williams
Attorney, Agent, or Firm—Haugen and Nikolai

[57] ABSTRACT

A zirconia oxygen sensor is disclosed which is especially designed for sensing respiratory gases on a breath-by-breath basis. In order to obtain a sufficiently high response time necessary for breath-by-breath gas analysis, a commercially-available zirconia ceramic element is dimensionally tailored to cooperate with a manifold member such that the volume of the gas being analyzed is extremely small, yet uniformly distributed over an internal surface of the zirconia cell. Cooperating with the zirconia cell and the manifold are a set of spring contacts which perform the dual function of providing an electrical terminal and acting as a gas-type seal when the manifold is compressed against the end of the cell.

9 Claims, 1 Drawing Sheet

ZIRCONIA CELL O₂ SENSOR FOR RESPIRATORY GAS ANALYSIS

BACKGROUND OF THE INVENTION

1. Field of the Invention

This invention relates generally to the design of an oxygen sensor and more particularly to a zirconia cell oxygen sensor especially designed for use in monitoring respiratory gases and providing an indication of the concentration of oxygen in the respiratory gas on a breath-by-breath basis.

II. Discussion of the Prior Art

In the Anderson et al U.S. Pat. No. 4,463,764, which is assigned to the assignee of the present invention, there is described a cardiopulmonary performance analyzer utilizing distributed processors for controlling the sensing, measurement, computation and display of a wide variety of metabolic parameters on a breath-by-breath basis. One of the components used in that system is an oxygen analyzer. It incorporates a slip cast zirconia cell with hand-painted electrodes. This method of manufacture is very labor-intensive and, therefore, expensive. In addition, the dimensional stability of the cell at the operating temperatures involved is somewhat poor, making it difficult to keep the sample volumes either low or uniform.

It is well known in the art that if a difference in the partial pressure of oxygen exists across a heated $ZrO_2$ ceramic stabilized by $Y_2O_3$, a voltage proportional to the log of the ratio of the partial pressures will be produced in accordance with the Nenst equation. A platinum or other suitable conductive coating on each side of the element provides a means for reading the voltage. Cells of this type are widely used in modern automobiles employing pollution control systems. By placing a zirconia cell in the exhaust manifold of an internal combustion engine, the cell is heated by the hot exhaust gases and is capable of providing a voltage signal indicative of the amount of oxygen present in the exhaust stream. Given the millions of automobiles produced each year and the need to periodically replace the oxygen sensor in older automobiles, zirconia cells for automotive use are produced in vast quantities and at relatively low prices. Thus, a significant cost reduction could be realized if commercially-available automotive zirconia cell oxygen sensors could be made to function reliably in a respiratory gas analyzer where the response time of the cell would have to accommodate real-time, breath-by-breath changes in oxygen concentration.

It is accordingly a principal object of the present invention to provide an improved, low-cost oxygen analyzer for use in respiratory gas analysis systems.

Another object of the invention is to provide a zirconia cell-type oxygen analyzer providing a rapid response to a step change in oxygen concentration of a sample gas at a low volume flow rate.

Yet another object of the present invention is to provide a means whereby a conventional zirconia cell designed for automotive applications can be adapted to a biomedical application involving extremely low sample gas flow rates while providing the requisite fast response times to changes in oxygen concentration.

SUMMARY OF THE INVENTION

The foregoing features and advantages of the invention are achieved by providing an electrical heating element having a cavity therein for receiving a zirconia element in the form of a hollow cone. A manifold member is provided having a cone-shaped manifold extension or probe having a longitudinal bore therethrough, the exterior profile of the probe fitting within the interior of the cone-shaped zirconia element with only an extremely small clearance (less than 0.02 cc) between the two. The gas sample is coupled to the longitudinal bore extending through the center of the manifold's probe and a negative pressure is created at the base of the zirconia cone. Hence, the gas sample being introduced and preheated through the central bore of the probe flows back over the exterior of the probe and the interior surface of the zirconia cell. Because of the close tolerance between the exterior surface of the probe and the interior hollow surface of the cell, a very low sample flow rate is maintained, yet it is spread uniformly over the interior surface of the cell.

The platinum electrode surfaces on the interior and exterior of the zirconia cone are connected by conductive traces to the base of the cone. Disposed between the base of the cone and the header are a pair of annular spring contacts which perform the dual function of providing an electrical connection to the zirconia cell from the voltage sensing device employed and, at the same time, function as a gas-tight seal between the manifold and the hollow interior of the zirconia cone. The seal remains effective throughout the substantial temperature range to which the assembly is subjected.

DESCRIPTION OF THE PREFERRED EMBODIMENT

Figure 1:
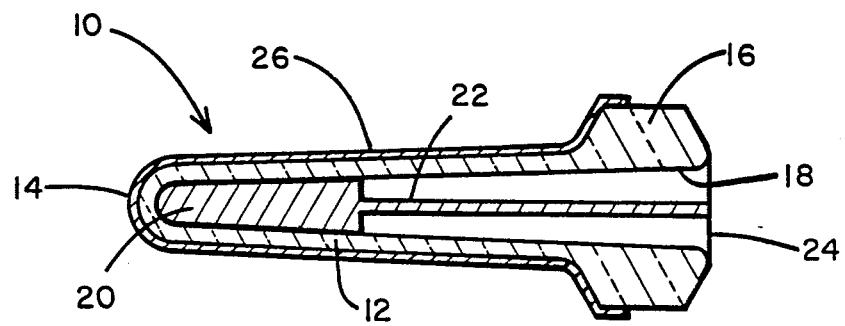
FIG. 1 is a cross-sectional view of a conventional zirconia cell used in the pollution control systems of many present-day automobiles.

Referring first to FIG. 1, there is illustrated a cross-sectional view of a stabilized zirconium oxide (zirconia) cell especially designed for automotive applications. The stabilized zirconium oxide ceramic material is molded in the form of a cone segment 12 having a rounded closed end 14 and an integrally formed cylindrical base 16. The cell 10 has a conical bore 18 creating a hollow interior. A platinum coating is painted, sprayed or otherwise formed or deposited on the interior wall surface as indicated by the shaded area 20 in FIG. 1 and a conductive trace 22 connects the conductive coating 20 to the rim of the base 24. In a somewhat similar fashion, a conductive coating, preferably of platinum, is deposited on the exterior surface of the ceramic element and is identified by numeral 26. The thickness of this coating 26 is exaggerated in FIG. 1 to render it more visible.

The $ZrO_2$ stabilized by $Y_2O_3$ ceramic comprises a solid electrolyte which exhibits ion conductivity between the conductive coatings 20 and 26. Gas having a known oxygen content is present as a reference gas on one side of the ceramic partition and the sample gas in which oxygen is present in an unknown concentration is present on the other side of the barrier. When the ceramic element is heated to a predetermined temperature, a potential difference is established between the two electrode coatings, producing a potential across the solid electrolyte which is transported by the oxygen ions in the solid electrolyte. This potential has a magnitude which is proportional to the log of the ratio of the oxygen concentrations on the two sides of the partition and, hence, it is possible to calculate the unknown oxygen concentration.

In the automotive application, a typical exhaust gas flow is 2000 l/min. This assumes a 2.0 liters displacement, 4 cylinder engine operating at 4000 rpm. The reference gas is introduced into the interior of the cell. No attempt is made to minimize the volume of the interior. There is no active method of exchanging the gas (air). The exterior of the cell is extended into the exhaust stream near the engine and is protected by a louvered shield. Engine exhaust is the only source of heat for raising the cell to an effective operating temperature.

Figure 2:
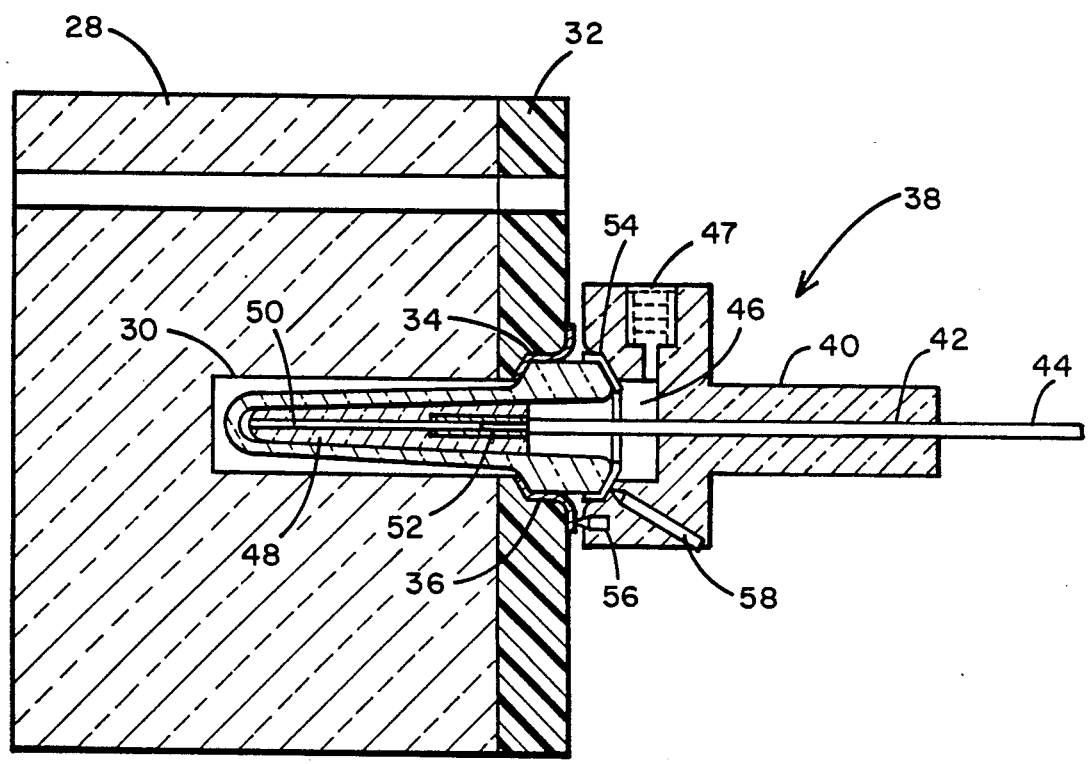
FIG. 2 is a cross-sectional view showing the manner in which the zirconia oxygen sensing element of FIG. 1 can be made to operate in a respiratory gas analyzing system.

Referring next to FIG. 2, an explanation will now be presented on how, in accordance with the present invention, the automotive zirconia cell of FIG. 1 can be adapted for use in a biomedical application where fast response times at relatively low sample gas flow rates are a requirement. Indicated by numeral 28 is an electrically heated furnace in the form of a cylindrical block having a central cavity 30 formed therein. The furnace is capable of creating and maintaining a predetermined high temperature, typically in the range of from 500° C. to 850° C. within the cavity 30. The furnace is affixed to a mounting plate 32. Formed in the mounting plate 32 is a socket 34 into which is fitted a first annular spring clip 36. When the zirconia cell 10 is inserted into the cavity 30, the spring clip 36 engages the conductive coating 26 on the outer surface of the cell and serves as a first electrical contact.

The oxygen sensor of the present invention further includes a manifold member indicated generally by numeral 38 which comprises a ceramic body 40 having a longitudinal bore 42 formed therethrough for receiving a sample gas inlet tube 44 therein.

Also formed in the manifold block 40 is a counterbore defining an annular cavity 46 which is in fluid communication with a vacuum port 47 formed transversely in the block. The sample gas inlet tube 44 extends beyond the cavity 46 and fitted onto the distal end of the tube 44 is a manifold extension comprising a conical probe 48. More particularly, the conical probe 48 includes a longitudinal bore 50 extending completely through the center thereof and which is dimensioned to fit over the end of the gas inlet tube 44 so as to be supported thereby.

The outside dimensions of the conical probe 48 are such that it conforms closely to the conical interior wall of the zirconia cell 10 with only a slight predetermined clearance between the two. The trapped volume between the exterior surface of the probe 48 and the interior surface of the cell 10 may typically be less than 0.02 cc which is very small when it is considered that the effective surface area of the zirconia cell is about 1 sq. cm.

It should also be mentioned at this point that the probe 48 is preferably but not necessarily formed from a machineable ceramic having a bulk coefficient of expansion equal to or slightly less than that of the zirconia cell such that when the assembly is heated to its operating temperature, the clearance between the exterior of the probe and the interior of the zirconia cell will be maintained over the active portion of this cell covered by the platinum electrode 20.

To provide support for the cell 10 while still allowing the gas sample to be drawn through the inlet tube 44, thence through the bore 50 in the probe 48 and back through the annular flow passage between the cell's interior wall and the exterior surface of the probe 48 under the influence of a vacuum source coupled to the manifold port 47, the surface of the probe is ground flat at 90° spaced intervals around the circumference as at 52. These flats provide a gas passage at the location along the probe where a zero clearance otherwise exists.

A second annular spring clip 54 surrounds the end of the base 24 of the zirconia cell 10 so as to make electrical contact with the trace 22 (FIG. 1) when the furnace block 28 containing the zirconia cell is clamped into resilient engagement with the manifold block 40. Quick-release, spring-loaded fasteners (not shown) are used to releasably secure the mounting plate 32 to the housing fixedly supporting the manifold 38 so as to bias the annular spring contacts 34 and 54 against the conductive traces on the zirconia cell and to compress the spring contact 54 in sealing relation to the manifold 40. This accommodates any dimensional changes as the materials become heated.

The manifold extension probe 48 is designed so that the cross-sectional area of the gap between the manifold extension and the zirconia cell are very nearly a constant. This assures a uniform gas velocity and flow within the cell. It is also designed such that the gas velocity within the cell and the gas velocity in the sample line 44 remain nearly identical so as to preserve history of the oxygen contact of the sample as it passes through the sample line.

First and second spring-loaded pin contacts 56 and 58 are mounted in bores drilled into the manifold block 40 so as to engage the conductive spring clips 36 and 54, respectively. Electrical leads (not shown) then couple the spring-loaded pin contacts 56 and 58 to the voltage measuring circuit with which the oxygen sensor of the present invention is to be used.

In that the sample gas is introduced through the tube 44 and the lumen 50 of the probe 48 before it is allowed to pass over the active surface of the zirconia cell, the gas sample becomes preheated before contacting the cell, thus inhibiting any tendency for the gas sample to alter the temperature of the cell. By utilizing a very small internal diameter gas inlet tube 44 and a correspondingly small longitudinal bore 50 in the probe 48, a high resistance is presented to any pressure surges in the system. Hence, the voltage read out from the zirconia cell remains substantially insensitive to transient pressure changes.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. Apparatus for sensing the partial pressure of oxygen in a gaseous mixture comprising, in combination:
(a) an electrical heater having a cavity therein;

(b) a conical zirconia ceramic element having an internal bore defining a lumen with a closed distal end and an open proximal end, the wall defining said lumen being of generally uniform thickness and having a conductive coating on opposed internal and external surfaces thereof;

(c) a manifold member including a probe conforming generally to the shape of internal bore and insertable into said lumen in said element to define a narrow annular flow path between the internal wall surface of said internal bore and the exterior of said probe, said manifold member including a longitudinal bore extending completely through said probe from a proximal end to a distal end;

(d) means for coupling a gas sample to be tested to said longitudinal bore of said manifold member at said proximal end of said manifold member, sand manifold member including means for coupling a source of negative pressure in fluid communication with said annular flow path to draw said gas sample through said longitudinal bore of said manifold member and uniformly over said surface of said wall via said annular flow path; and (e) means for conductively coupling said conductive coatings on the opposed surfaces of said wall to voltage measuring means.

2. The apparatus as in claim 1 wherein said conical zirconia ceramic element is generally conical over a majority of its length with an integrally formed cylindrical base at said proximal end.

3. The apparatus as in claim 2 wherein said manifold member is separable from said electrical heater and said ceramic element.

4. The apparatus as in claim 3 wherein said ceramic element is separable from said electrical heater.

5. The apparatus as in claim 2 wherein said means for conductively coupling comprises:

(a) a first annular spring contact surrounding said cylindrical base and conductively joined to said conductive coating on the exterior surface of said ceramic element;

(b) a second annular spring contact surrounding said cylindrical base and conductively joined to said conductive coating on the internal surface of said ceramic element; and (c) spring loaded pin contacts disposed in said manifold means for engaging said first and second spring contacts when said heating means containing said ceramic element in said cavity is fastened to said manifold member.

6. The apparatus as in claim 5 wherein said second spring contact creates a replaceable gas-tight seal between said manifold member and said ceramic element when said electrical heater containing said ceramic element in said cavity is fastened to said manifold means.

7. The apparatus as in claim 1 wherein said volume of said narrow annular flow path is in the range from about 0.01 cc to 0.03 cc.

8. The apparatus as in claim 1 wherein said electrical heater is capable of heating said ceramic element to a temperature in the range of from about 500° C. to 850° C.

9. The apparatus as in claim 1 wherein said gas sample, when passing through said longitudinal bore in said manifold member, is preheated by said electrical heater to inhibit cooling of said ceramic element as said gas sample flows through said annular flow path.

* * * * *